US008291519B2

(12) United States Patent
Arsenault et al.

(10) Patent No.: US 8,291,519 B2
(45) Date of Patent: Oct. 23, 2012

(54) BACK SUPPORT GARMENT APPARATUS

(76) Inventors: James Arsenault, East Williston, NY (US); Paul Iskyan, Manhasset, NY (US); Vijay Vad, New York, NY (US)

(*) Notice: Subject to any disclaimer, the term of this patent is extended or adjusted under 35 U.S.C. 154(b) by 0 days.

(21) Appl. No.: 12/983,831

(22) Filed: Jan. 3, 2011

(65) Prior Publication Data

US 2011/0172577 A1 Jul. 14, 2011

Related U.S. Application Data

(63) Continuation of application No. 12/079,161, filed on Mar. 25, 2008, now Pat. No. 7,882,574.

(51) Int. Cl.
*A41D 1/06* (2006.01)
(52) U.S. Cl. .............................. 2/227; 602/19
(58) Field of Classification Search .............. 2/228, 238, 2/79, 227, 46, 48, 50–51, 69, 92, 338, 310–317; 128/99.1, 100.1, 101.1, 102.1; 602/19
See application file for complete search history.

(56) References Cited

U.S. PATENT DOCUMENTS

| | | | | |
|---|---|---|---|---|
| 2,249,198 | A | * | 7/1941 | Carter ................................ 2/404 |
| 2,553,353 | A | * | 5/1951 | Binder et al. .................... 602/67 |
| 4,676,247 | A | * | 6/1987 | Van Cleve ..................... 607/112 |
| 4,836,194 | A | * | 6/1989 | Sebastian et al. ............... 602/19 |
| 4,972,832 | A | * | 11/1990 | Trapini et al. .................. 607/108 |
| 5,038,779 | A | * | 8/1991 | Barry et al. .................... 607/108 |
| 5,157,790 | A | * | 10/1992 | Aldridge ............................ 2/227 |
| 5,179,942 | A | * | 1/1993 | Drulias et al. ............. 128/101.1 |
| 5,205,815 | A | * | 4/1993 | Saunders ......................... 602/19 |
| 5,351,340 | A | * | 10/1994 | Aldridge ............................ 2/108 |
| 5,398,667 | A | * | 3/1995 | Witt ......................... 126/263.01 |
| 5,399,150 | A | * | 3/1995 | Saunders ......................... 602/19 |
| 5,403,271 | A | * | 4/1995 | Saunders et al. ................ 602/60 |
| 5,484,366 | A | * | 1/1996 | Wilkinson ..................... 482/105 |
| 5,533,961 | A | * | 7/1996 | Iwata ............................... 602/19 |
| 5,605,144 | A | * | 2/1997 | Simmons et al. ............. 126/204 |
| 5,611,084 | A | * | 3/1997 | Garry et al. ........................ 2/93 |
| 5,665,057 | A | * | 9/1997 | Murphy .......................... 602/19 |
| 5,716,388 | A | | 2/1998 | Petelle |

(Continued)

FOREIGN PATENT DOCUMENTS

EP 0636325 B1 3/1999

(Continued)

OTHER PUBLICATIONS

The Saunders Group, Inc., S'port All Back Support, 2006.

(Continued)

*Primary Examiner* — Tejash Patel
(74) *Attorney, Agent, or Firm* — Tiajoloff and Kelly LLP

(57) ABSTRACT

A one-piece back support apparatus comprises a belt portion being configured to provide back and abdominal support encircling a wearer's waist and a compression pants portion. The belt portion has a front portion, a back portion, a top portion, a bottom portion and an inner surface. The compression pants portion secured to the belt is configured to provide support for the wearer's pelvis, legs, and groin area. The inner surface of the belt has one or more pack support portions with slots for receiving one or more gel packs so as to maintain contact between the gel packs and the wearer's back. Slots in the belt portion may accommodate vertically extending inserts of rigid plastic to reinforce the belt portion over the lumbar region of the wearer.

20 Claims, 7 Drawing Sheets

U.S. PATENT DOCUMENTS

| | | | |
|---|---|---|---|
| 5,928,275 A | 7/1999 | Yates et al. | |
| 6,006,363 A | 12/1999 | Karlin | |
| 6,108,819 A | 8/2000 | DeBaene et al. | |
| 6,119,275 A | 9/2000 | Goyal | |
| 6,205,591 B1 | 3/2001 | Wheeler et al. | |
| 6,367,086 B1 | 4/2002 | Woodard | |
| 6,585,673 B1 | 7/2003 | Bass | |
| 6,656,210 B1 | 12/2003 | Plewes | |
| 7,882,574 B2 * | 2/2011 | Arsenault et al. | 2/227 |
| 2005/0090882 A1 | 4/2005 | Wei | |
| 2005/0268379 A1 | 12/2005 | MacGeorge | |

FOREIGN PATENT DOCUMENTS

| | | |
|---|---|---|
| JP | 2004229783 A | 8/2004 |

OTHER PUBLICATIONS

The Saunders Group, Inc., S'port Max Back Support, 2006.

Espacenet English Language Abstract for JP2004-229783, Aug. 19, 2004.

Scott Specialities, Inc., "PR* Pain Reliever", Jun. 2004.

* cited by examiner

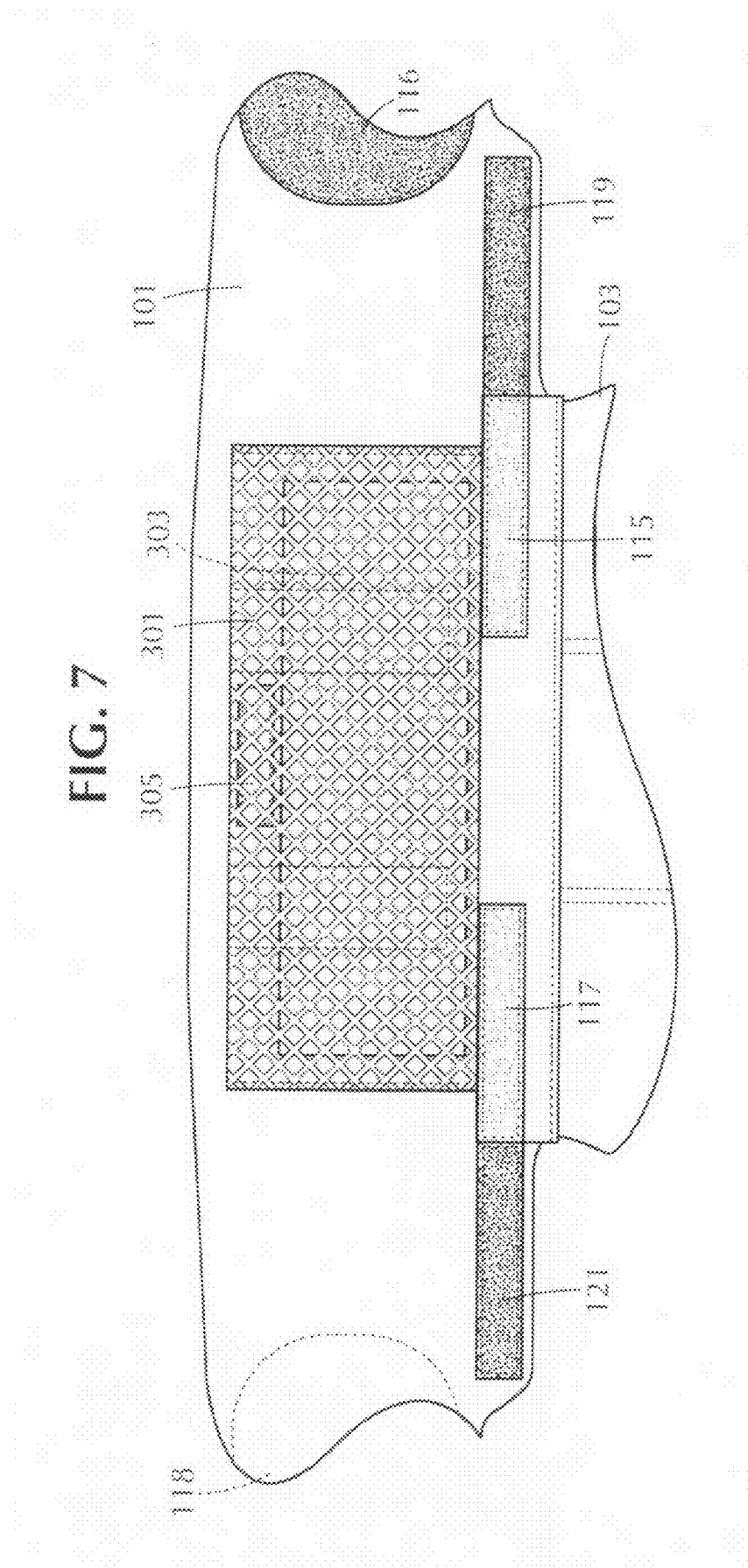

BACK SUPPORT GARMENT APPARATUS

RELATED APPLICATIONS

This application is a continuation of U.S. patent application Ser. No. 12/079,161, filed Mar. 25, 2008, which is herein incorporated by reference.

FIELD OF THE INVENTION

The present invention relates to back support garments, and more particularly to a one-piece support belt and compression pants apparatus.

BACKGROUND OF THE INVENTION

Millions of Americans suffer from back injuries and back pain, which can easily be aggravated by participation in athletic, physical, and even everyday activities. The lower back, or lumbar region, supports the weight of the upper body and is the most common site of back injuries. Treatment for back injuries often involves restoring strength to the back and preventing recurrence of the injury.

Back patients often wear back support garments to compress and restrict movement in the lumbar spine and surrounding muscles to prevent further back strain. There are many variations of compressive back supports in the prior art. These often consist of a back support device made from a stiff fabric configured to compress the wearer's waist area.

Although several back supports exist in the prior art, most existing back support apparatuses provide compressive support only to the lumbar area and fail to extend support to the tailbone region of the spine and its surrounding muscles, which are also vulnerable to injury. Furthermore, back supports of the prior art also do not provide adequate compressive support to a wearer's leg and groin muscles. In addition, they do not provide for localized therapeutic heating or cooling of the lumbar region.

SUMMARY OF THE INVENTION

It is accordingly an object of the present invention to provide a back support apparatus that does not have the drawbacks of the prior art.

An object of the present invention is to provide a one-piece apparatus that evenly distributes forces applied on the body during athletic, physical and every day activity, in particular those applied during twisting or forward bending movements, such as when swinging a golf club or skiing downhill, over a wearer's lumbar to mid-thigh regions, while simultaneously providing therapeutic heating and cooling benefits.

In accordance with an aspect of the present invention, a back support garment for a wearer includes a compression pants portion configured to provide support for the wearer's pelvis, legs, and groin area. A belt portion attached fixedly to and extending upwardly from the compression pants portion and has a rear portion configured to support to a lumbar and an abdominal area of the wearer. The belt portion is attached to the pants portion so as to align its rear portion with the lumbar region of the wearer.

In another embodiment of the invention, the back support garment has a pack support structure with one or more slots supporting therein one or more hot or cold packs adjacent an inner surface of the pack support structure. The belt portion is attached to the pants portion so as to align the pack support portion with a lumbar region of the wearer and to maintain temperature transferring contact between the inner surface of the belt portion adjacent the hot and cold packs and the wearer's lumbar region.

According to an aspect of the invention, the compression pants portion is shorts extending no lower than the thighs of the wearer. In another aspect of the invention, the compression pants portion extends past the wearer's knees.

In another aspect of the invention, a rear portion of the belt portion has an insert receiving structure with one or more slots supporting therein one or more inserts configured to provide further support for the wearer's back.

Other objects and advantages of the invention herein will become apparent in the specification below.

BRIEF DESCRIPTION OF THE DRAWINGS

FIG. 7 is an enlarged partial front view of another alternate embodiment of the present invention, showing the showing the pack support structure having only one slot for receiving hot or cold packs.

DETAILED DESCRIPTION

Figure 1:
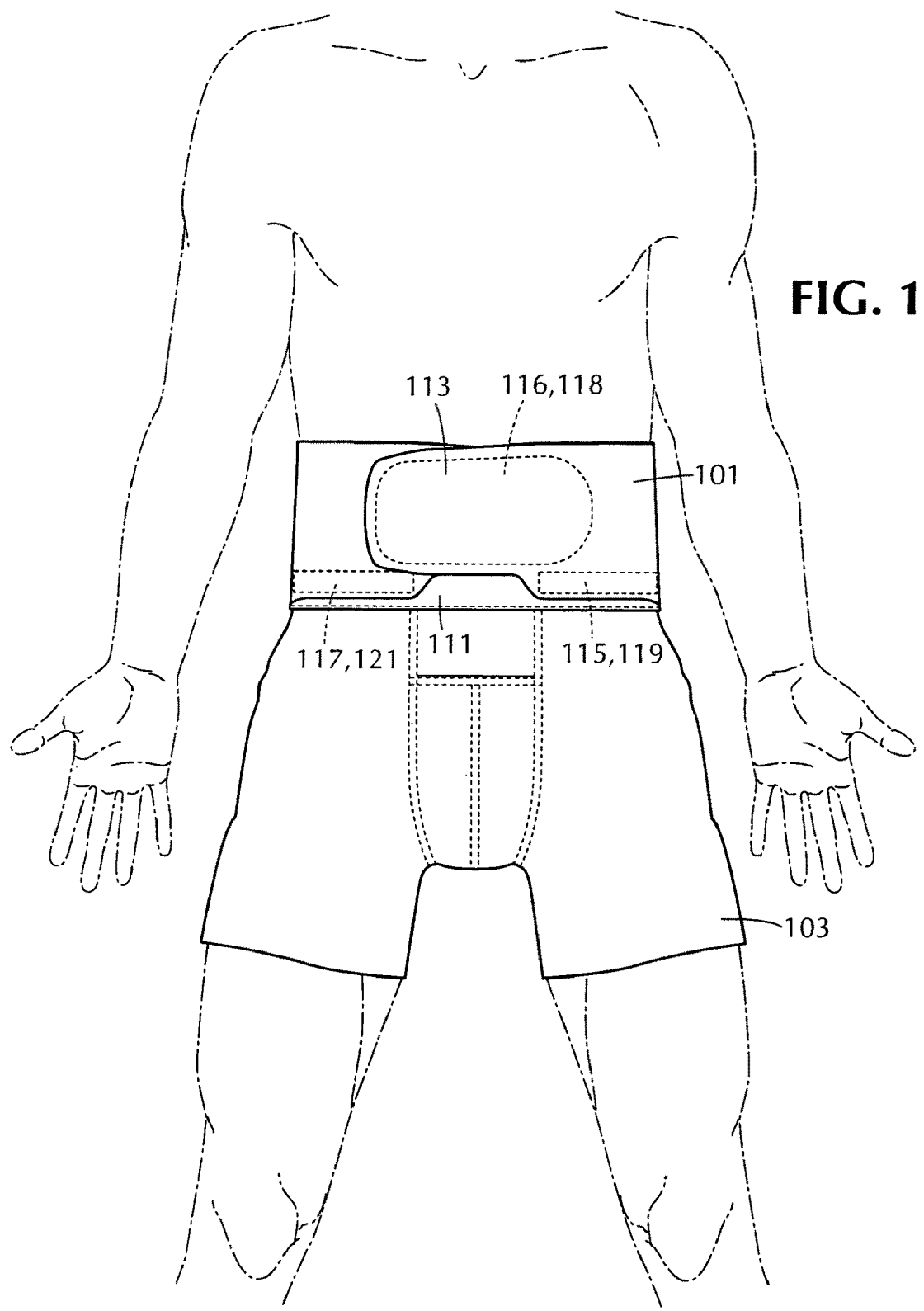
FIG. 1 is a front view of an embodiment of the support garment of the invention, as worn by a user.
Figure 2:
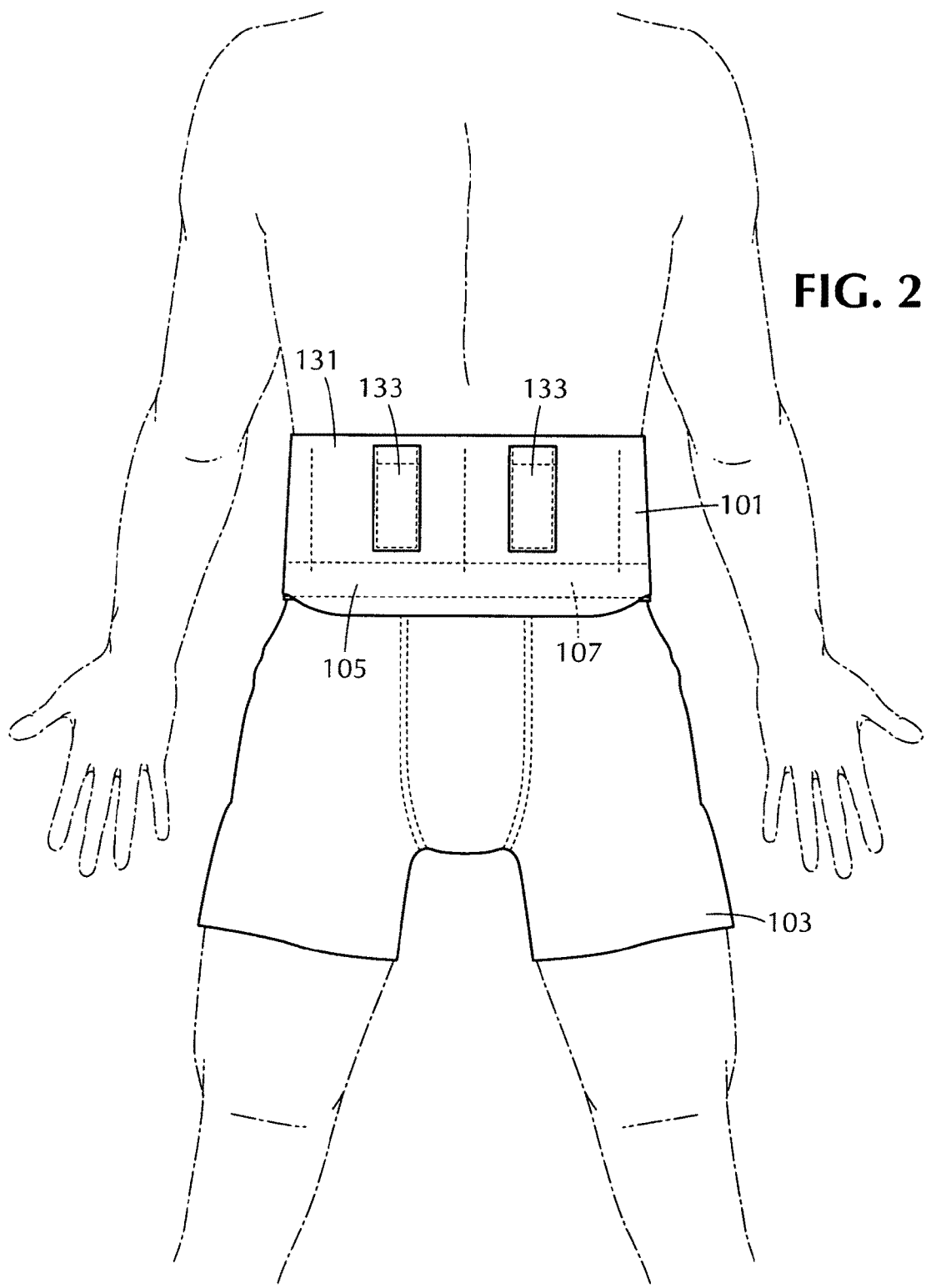
FIG. 2 is a back view of the support garment of FIG. 1.
Figure 3:
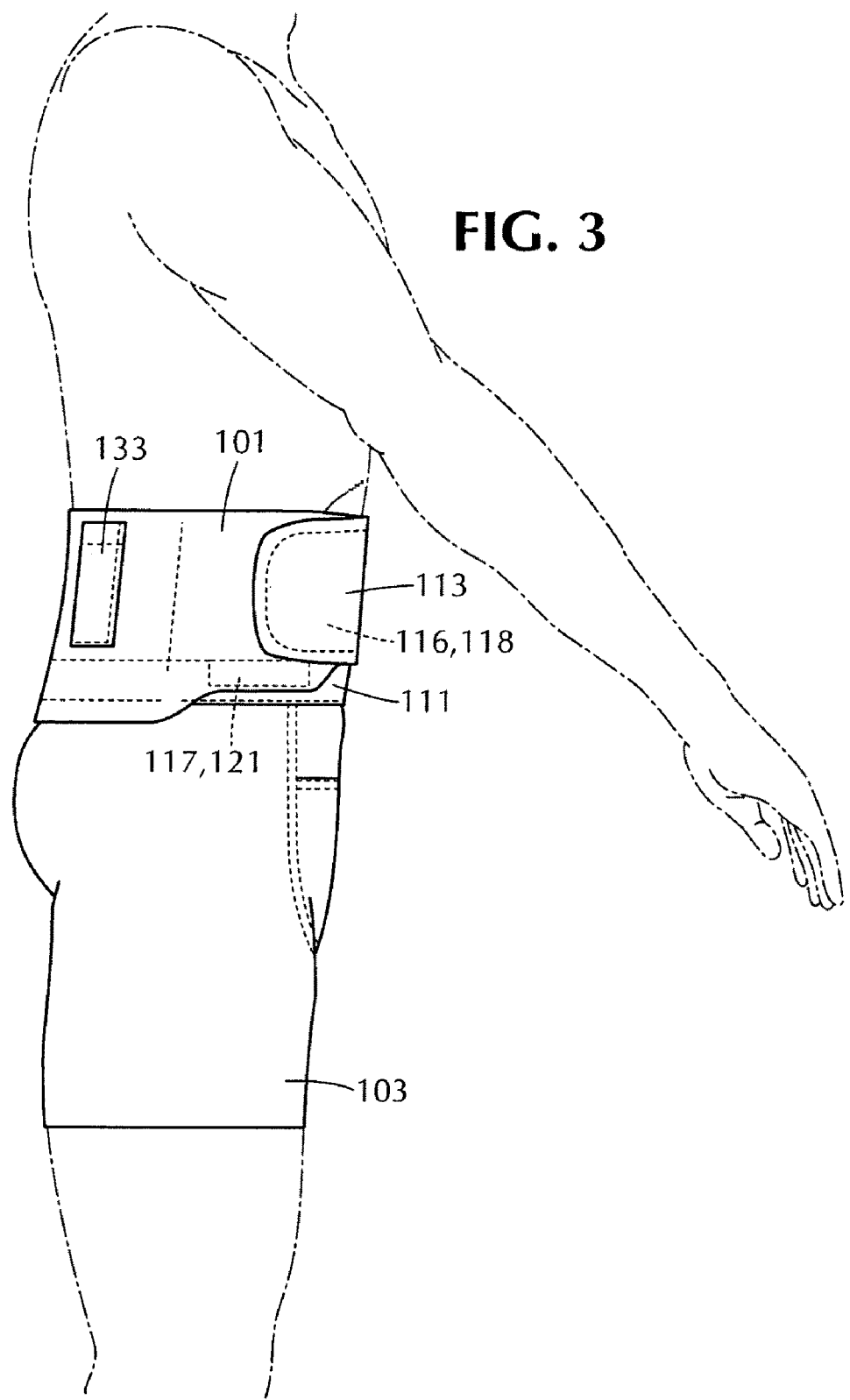
FIG. 3 is a left-hand side view of the support garment of FIGS. 1 and 2.

As best seen in FIGS. 1, 2 and 3, the present apparatus generally comprises a unitary garment having a belt portion 101 and a compression pants portion 103. Belt portion 101 encircles the waist of a wearer, and extends upwardly from the compression pants portion 103.

As shown in FIGS. 2 and 3, the rear portion 105 of the belt portion 101 is fixedly secured to a rear portion 107 of the pants portion 103, thus locating the belt of the user when wearing the pants portion 103, and preventing separation of the pants portion 103 from the belt portion 101 when the wearer moves. Securing the pants portion 103 and the belt portion 101 distributes the compressive support provided by the pants and the belt individually over the entire lumbar region extending from the wearer's waist to the wearer's tailbone area.

Figure 4:
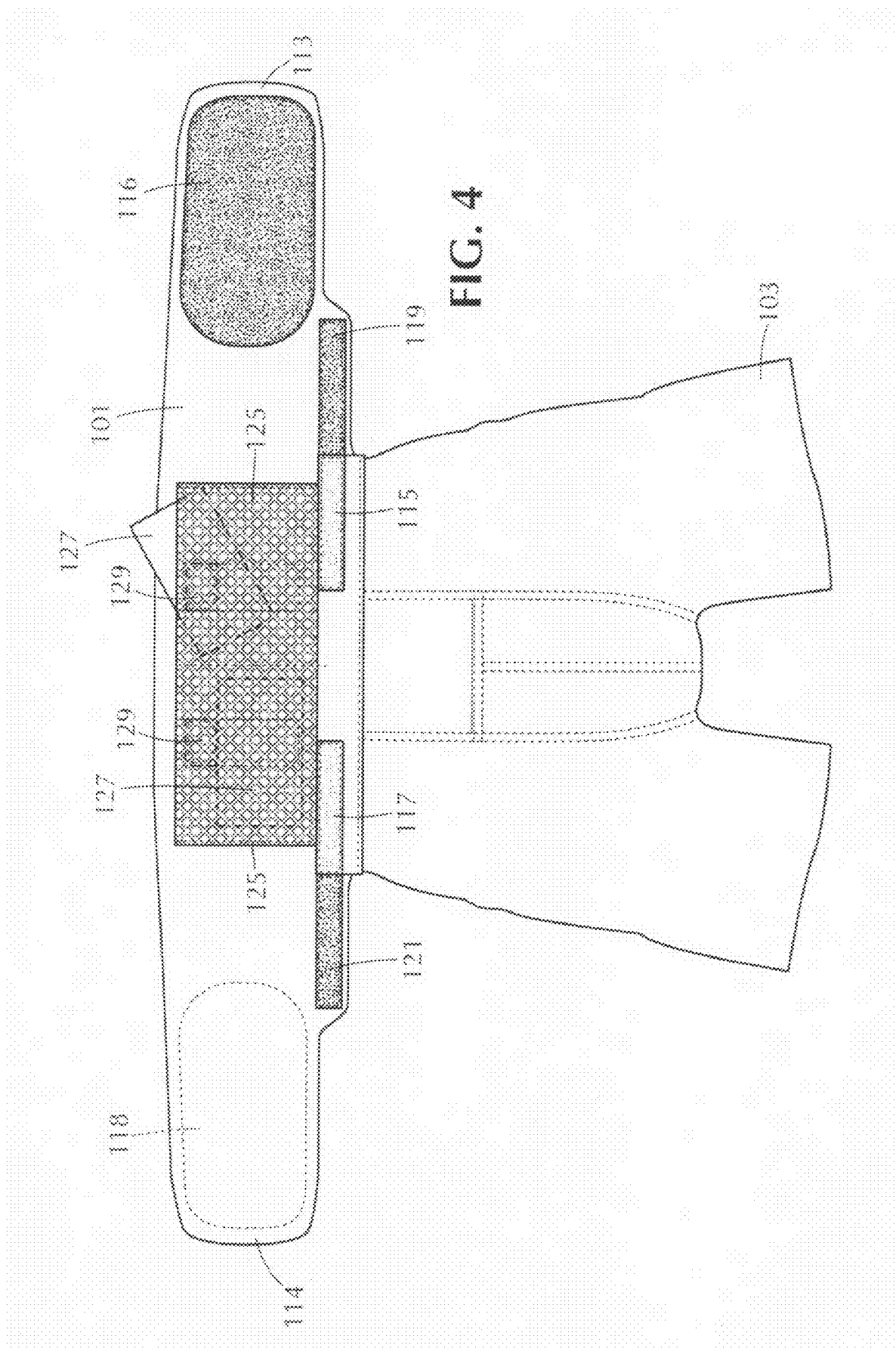
FIG. 4 is a front view of the garment of FIGS. 1-3 when not worn, showing the pack support structure having multiple slots for receiving hot or cold packs.
Figure 5:
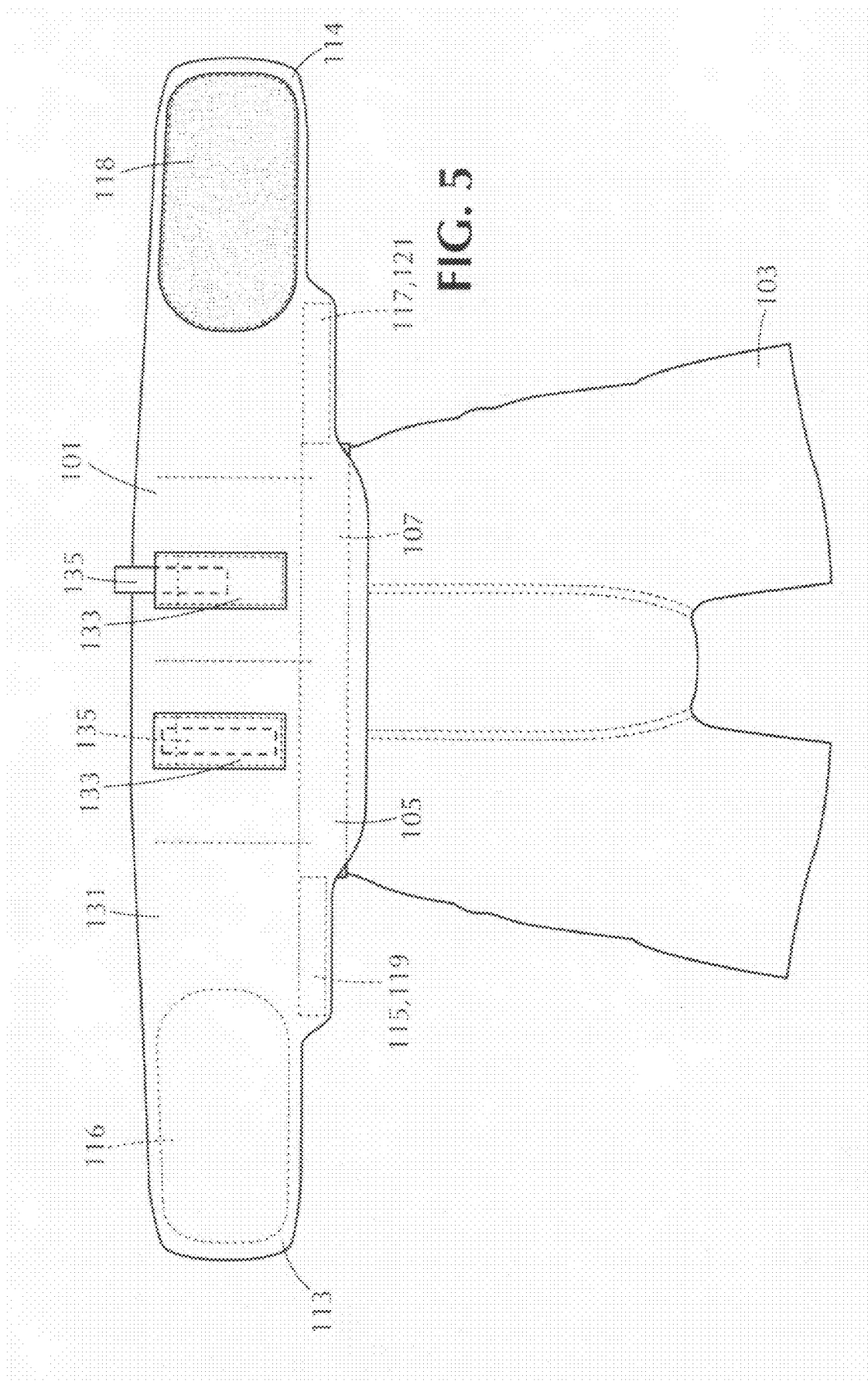
FIG. 5 is a back view of the garment as seen in FIG. 4.

Referring to FIG. 5, the rear portion 107 of the pants portion 103 and the rear portion 105 of the belt portion 101 are fixedly secured to each other, as by glue or stitching, while, as shown in FIG. 4, the forward waistband portion 111 of the pants portion 103 and the forward portion 113 of the belt portion 101 are configured so as to be releasably attachable to one another by releasable connection structures or means. These portions 111 and 113 are adjustably and releasably connected with each other so that the user can adjust a relative position of the forward waistband portion 111 of the pants portion 103 in relation to the forward portion 113 of the belt portion 101, so as to comfortably conform the garment to the wearer's body.

In the embodiment depicted in FIG. 4, the forward waistband portion 111 of the pants portion 103 has secured thereon one or more strips of a hook and loop fastening fabric strips 115 and 117, such as Velcro®. The unsecured bottom portions of the belt portion 101 are lined with complementary strips of hook and loop fastening fabric strips 119 and 121, respectively, extending circumferentially about the waist of the user and that releasably secure the forward portion 113 of belt portion 101 to forward portion 111 of pants portion 103, by co-acting securement of fabric strips 115 and 117 with fabric strips 119 and 121.

The compression pants portion 103 is constructed from a light-weight elastic material having the requisite stiffness and elasticity to compressively support the abdominal, groin and leg muscles of the wearer, while also being comfortable and providing ease of movement during athletic, physical or daily activity. Examples of materials which are suitable for these purposes include fabrics containing Lycra, Spandex, or a similar stretch material. In the preferred embodiment of the invention, the material further has moisture-wicking capabilities which further prevent chafing and allow for cooling of the covered muscles when the user is performing sweat-inducing activities.

In the preferred embodiment, the compression pants portion 103 is shorts that extend no lower than the thighs of the wearer, from the wearer's waist area to a mid or lower thigh position. This length provides compressive support to the wearer's abdominal, groin, and quadriceps muscles, and is suitable for wear during most athletic, physical, or everyday activities.

The belt portion 101 is constructed from a stiff fabric to enhance stabilization and support of the lumbar region, while also allowing the wearer enough freedom of movement to engage in athletic, physical or daily activity requiring twisting or bending of the spine. Synthetic laminated or woven stretchable fabrics, such as Neoprene, manufactured by the DuPont Corporation, are desirable due to their stiffness, flexibility, and insulating properties. In the preferred embodiment of the invention, the material is a permeable or breathable fabric that also wicks perspiration away from the skin for enhanced comfort, such as Breathoprene®, by AccuMED Technologies, Inc. The material forming the belt portion is sufficiently thin so as to make the belt invisible when worn under other garments or athletic attire. Preferably, the overall thickness of the belt is between 1 mm and 5 mm, as this provides the requisite amount of lumbar support, while maintaining the invisibility of the belt under the wearer's outer garments.

Use of the above materials is desirable for their mechanical properties, but such material may cause sticking of the wearer's outer garments to the belt. Accordingly, the outer surface of the belt is covered by a thin, smooth fabric such as Nylon so as to minimize friction between the user's outer clothing and belt during periods of contact, and to prevent bunching of the wearer's outer garments around the belt. The fabric covering the outer surface of the belt should be so thin that it has no, or minimal effect on the overall thickness of the belt.

As best seen in FIGS. 4 and 5, belt portion 101 has a first and second ends 113 and 114, that are each configured so as to be releasably attachable to each other, allowing the wearer to fasten the belt portion 101 tightly around the wearer's waist in a range of possible waist sizes, so as to wear the belt snugly as depicted in FIGS. 1, 2 and 3. The first end 113 of the belt portion 101 has secured thereon a patch 116 of hook and loop type fastening fabric, and the second end 114 of the belt portion 101 is lined with a complementary co-acting patch 118 of hook and loop type fastening fabric. The patches 116 and 118 are large enough about the waist of the wearer, and configured to be releasably secured to each other in a variety of waist size positions and with some varying angulation, if desired. Alternatively, the entire inner surface 123 of the belt can be lined with the loop material so as to co-act with a patch of hook fabric secured onto the second end 114 of the belt.

Other types of fastening mechanisms, such as a buckle or lace-up configuration having openings in it may also be used to adjustably secure the belt portion 101 around the waist of the user.

As shown in FIG. 4, the inner surface 123 of the belt portion 101 includes two pack support structures 125 with one or more slots therein configured to receive therapeutic hot or cold packs 127. The pack support structures 125, which are secured to the inner surface 123 of the belt portion 101 by glue or stitching, are positioned so as to maintain temperature transferring contact between the inner fabric of the support structures 125 adjacent the inserted therapeutic packs 127 and the lumbar region of the wearer when the belt portion 101 is fastened around the wearer's waist. Preferably, the therapeutic packs 127 are sized so as to cover the wearer's entire back waist region when inserted into the slots, including the spinal cord and its surrounding muscles.

The pack support structures 125 are preferably formed from a single piece of waterproof and breathable material such as nylon, which is sufficiently strong to accommodate the weight of the pack without tearing, but which is thin enough so that the hot or cold effects of the packs can instantly be felt by the wearer. A mesh material, as shown, may be employed for the inner fabric of the support structures 125, or a piece of continuous material may be used.

As shown in FIG. 4, the inner fabric of the pack support structures 125 and the inner surface 123 of the belt portion 101 adjacent the therapeutic packs 127 have secured thereon strips of co-acting hook and loop fastening fabric 129, thereby allowing the wearer to close the openings formed by the pack support structures 125 and firmly position the get packs 125 in the pack support structures. Other types of closure mechanisms, such snaps or buttons, may also be used to close the openings formed by the pack support structures.

A wide variety of therapeutic hot and cold packs are commercially available for use with the present invention. Ice packs, for example, are often distributed as pre-sealed plastic sacks containing refrigerant gels or liquids, but can also be homemade variants made from suitable plastic bags filled with crushed or cubed ice. Heat packs are also widely available as microwavable plastic sacks containing a liquid or a gel with a high specific heat. Commercially available electric heating and cooling packs may also be used.

As best shown in FIG. 5, the outer surface 131 of the rear portion 105 of the belt portion 101 is provided with one or more additional insert support structures 133 secured fixedly thereon and configured to removably receive one or more rigid inserts 135. Preferably, an insert support structure 133 is positioned in the belt portion 101 so that when worn, the inserts 135 each align spaced on each side adjacent the user's spinal cord so that the inserts 135, when placed in the insert support structures 133, provide additional support to the spinal cord and its surrounding muscles, or help the wearer maintain proper back alignment.

A user may choose not to use inserts 135 with the slots in pack support structures 133, since the inserts 135 further restrict the range of movement of the user's spine, potentially making it difficult for the wearer to engage in certain athletic, physical or everyday activities. This embodiment relying on the inserts may be desirable for individuals nursing a more serious back injury requiring extra support. The removable nature of the rigid inserts 135 means that the support garment can be selectively used with or without support, depending on the specific requirements of the selected activity of the user.

The inserts 135 are formed from a lightweight material, such as plastic or rubber, and have a variable resistance to bending that is determined by the insert's thickness and the properties of the material from which the insert 135 is formed. The inserts 135 are sufficiently thin so as to be less visible when the garment is worn under other clothing, and are of a sufficient length so as to extend over the lumbar region of the wearer extending above the pelvis. The insert support structures 133 receiving the inserts 135 are each preferably formed from a single piece of material having sufficient strength to accommodate the weight of the insert 135, and to secure the insert 135 in stiffening support of the belt portion 101.

Figure 6:
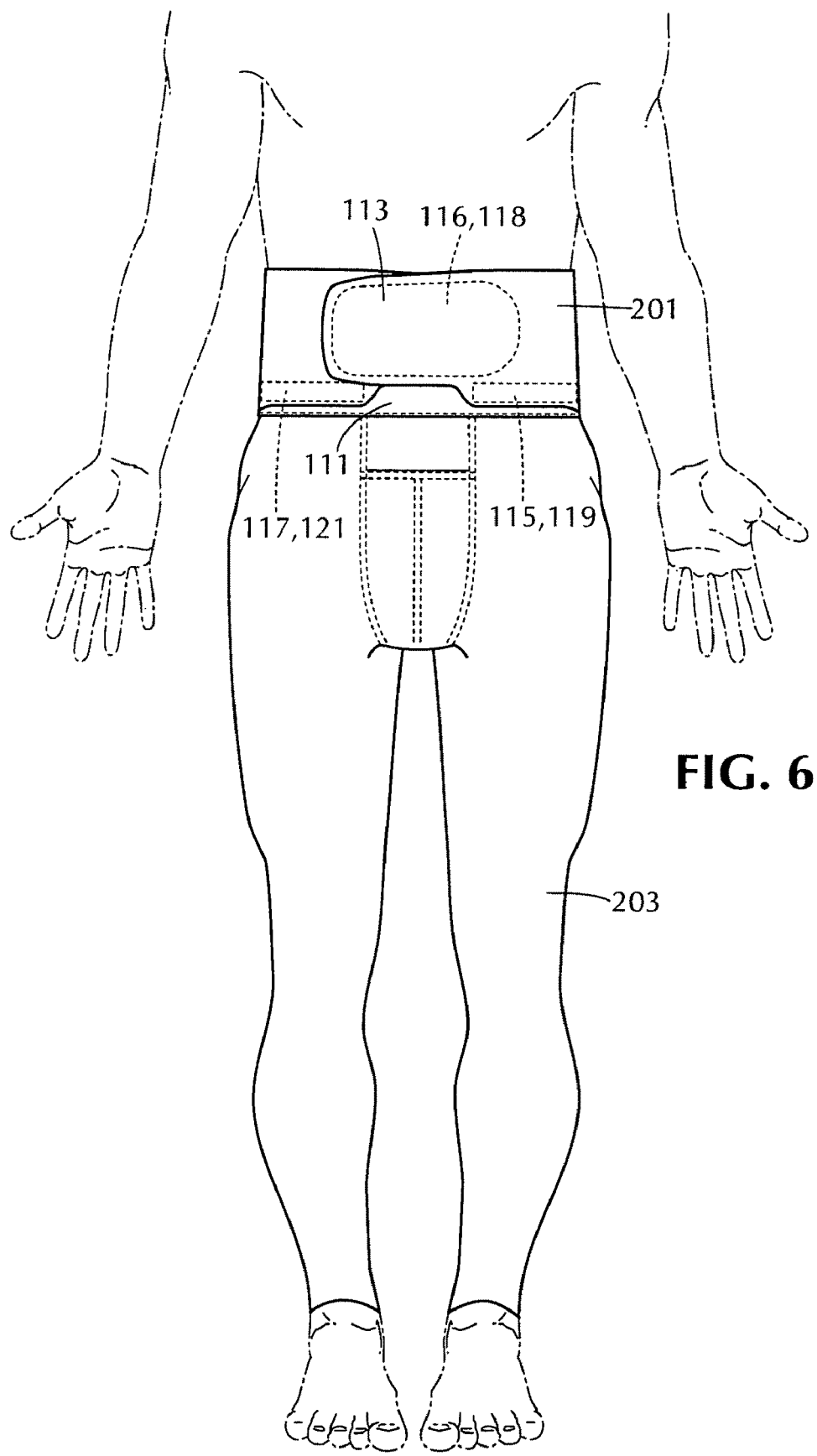
FIG. 6 is a front view of an alternate embodiment of the present invention, as worn by a user.

In an alternate embodiment, which is depicted in FIG. 6, compression pants portion 203 extends downward past the wearer's lower thigh, so as to also cover a user's knees and calves. This embodiment also provides added warmth and support to a wearer's calf muscles, and is preferable for wear during cold weather activities, such as skiing, skating, or snowmobiling. Belt portion 201 is configured similarly to the embodiment of FIGS. 1 to 5 and the same reference numbers are used for corresponding parts thereof.

In a further alternate embodiment of the invention, shown in FIG. 7, the pack support structure 301 has a single interior space extending laterally substantially across the back of the user. This structure 301 is configured to receive and support therein a single, elongated therapeutic hot or cold pack 303 that is sized so as to cover the wearer's entire back waist region in the interior space. The inner fabric of the pack support structure 301 and the inner surface 123 of the belt portion 101 adjacent the elongated hot or cold pack 303 are releasably secured to each other by strips of co-acting hook and loop fastening fabric 305 thereon, so as to allow the wearer to close the space 303.

The materials and construction of the belt 101 is otherwise similar to that of the belt portion 101 of the preferred embodiment, and similar reference characters are used for complementary parts.

It will be understood that the invention herein extends well beyond the embodiments of the disclosure, and the terms used in this specification should be understood to be language of description, not limitation, as those of skill in the art with this specification before them will be able to make changes and modifications therein without departing from the spirit of the invention.

What is claimed is:

1. A back support garment for a wearer, said garment comprising:
   a compression pants portion being configured to provide support for the wearer's pelvis, legs, and groin area; and
   a belt portion attached fixedly to and extending upwardly from the compression pants portion;
   said belt portion being configured to support a lumbar and an abdominal area of the wearer, and including a rear portion configured to overlay and support the lumbar portion of the wearer;
   said belt portion being attached to said pants portion so as to align the rear portion with the lumbar region of the wearer.

2. The back support garment of claim 1, further comprising a pack support structure supporting therein one or more hot or cold packs adjacent an inner surface of said belt portion,
   said belt portion being attached to said pants portion so as to align the pack support portion with the lumbar region of the wearer and to maintain temperature transferring contact between an inner surface of the pack support structure adjacent said hot and cold packs and the wearer's lumbar region.

3. The back support garment of claim 1, wherein said rear portion of the belt portion includes rigidifying structure.

4. The back support garment according to claim 1, wherein the rear portion of said belt portion has an insert receiving structure supporting therein one or more inserts being configured to provide further support for the wearer's back, said inserts being composed of material having a resistance to bending greater than that of the rear portion of the belt portion.

5. The back support garment of claim 4, wherein said insert support structure has slots receiving said inserts, and said inserts being removable by the wearer by sliding out of the associated slot.

6. The back support garment according to claim 1, wherein said compression pants portion is shorts extending no lower than the thighs of the wearer.

7. The back support garment according to claim 1, wherein said compression pants portion extends downwardly past the wearer's knees.

8. The back support garment according to claim 2, wherein a rear portion of said compression pants portion is fixedly secured to the rear portion of said belt portion adjacent the hot or cold packs.

9. The back support garment according to claim 1, wherein said belt portion comprises a first end and a second end that are releasably attachable to each other so as to adjustably secure said belt tightly around the wearer's waist.

10. The back support garment according to claim 9, wherein first and second ends of said belt are arranged in a front portion of said belt.

11. The back support garment according to claim 9, wherein said first end of said belt has hook and loop fastener material fixedly secured thereto and said second end of said belt has complementary hook and loop fastener material fixedly secured thereto so that said first end is releasably and adjustably attachable to said second end.

12. The back support garment according to claim 1, wherein said pants portion has a forward waistband portion that is releasably attachable to a portion of said belt portion to adjust a relative position of the pants portion to the belt portion.

13. The back support garment according to claim 12, wherein said forward waistband portion of said pants portion has hook and loop fastener fabric fixedly secured thereto and said portion of said belt portion has complementary hook and loop fastener material fixedly secured thereto to adjust a relative position of the pants portion to the belt portion.

14. The back support garment according to claim 4, wherein said inserts are plastic.

15. The back support garment according to claim 1, wherein said belt portion is made from a breathable and semi-rigid material.

16. The back support garment according to claim 1, wherein said compression pants portion is made from a material containing an elastic fabric so that the compression pants portion compresses the wearer's body when thereon.

17. The back support garment according to claim 1, wherein said compression pants portion is made is made from a material having moisture-wicking properties.

18. The back support garment according to claim 1, wherein said compression pants portion is made is made from nylon fabric.

19. The back support garment according to claim 1, wherein surfaces of said belt portion are lined with a fabric having a low coefficient of friction.

20. The back support garment according to claim 1, wherein said belt portion has a thickness between 1 mm and 5 mm.

* * * * *